(12) United States Patent
Janik et al.

(10) Patent No.: US 10,716,883 B2
(45) Date of Patent: Jul. 21, 2020

(54) METHOD AND APPARATUS FOR INTERMITTENT PULSATING PROPORTIONING OF A DIALYSIS FLUID MIXTURE

(71) Applicant: B. BRAUN AVITUM AG, Melsungen (DE)

(72) Inventors: Waldemar Janik, Melsungen (DE); Kai-Uwe Ritter, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 329 days.

(21) Appl. No.: 15/963,565

(22) Filed: Apr. 26, 2018

(65) Prior Publication Data
US 2018/0311429 A1     Nov. 1, 2018

(30) Foreign Application Priority Data
Apr. 27, 2017  (DE) .................. 10 2017 109 127

(51) Int. Cl.
*A61M 1/16*          (2006.01)
(52) U.S. Cl.
CPC ........ *A61M 1/1603* (2014.02); *A61M 1/1607* (2014.02); *A61M 1/1656* (2013.01); *A61M 2205/18* (2013.01); *A61M 2205/3317* (2013.01); *A61M 2205/3372* (2013.01)
(58) Field of Classification Search
CPC .............. A61M 1/1603; A61M 1/1607; A61M 1/1656; A61M 2205/18; A61M 2205/3317; A61M 2205/3372
See application file for complete search history.

(56) References Cited

U.S. PATENT DOCUMENTS

| 2014/0220699 A1 | 8/2014 | Pudil et al. |
| 2016/0000990 A1 | 1/2016 | Ritter |
| 2018/0140762 A1 | 5/2018 | Kopperschmidt |

FOREIGN PATENT DOCUMENTS

| EP | 2962711 A1 | 1/2016 |
| WO | 2016169642 A1 | 10/2016 |

OTHER PUBLICATIONS

European Search Report for European Application No. 18 169 603.0, dated Apr. 9, 2018, with English translation—7 pages.

*Primary Examiner* — Dirk R Bass

(57) ABSTRACT

An apparatus and a method for preparing dialysis fluid for use in extracorporeal blood treatment, wherein the apparatus includes a main line for the supply of water in the course of which each of an acid fluid and a basic fluid is fed at a particular dosage, wherein the dosage is set by a control and regulating unit as a function of at least one chemical and/or physical parameter of the water-fluid mixture and the parameter is detected by a measuring instrument wherein a first measuring instrument is arranged at a section of the main line located downstream of each of the feeding point for the acid fluid and the feeding point for the basic fluid and the control and regulating unit at least temporarily controls the feeding of the acid and basic fluids such that over a predetermined period of time or a predetermined interval only one from among the acid and basic fluids is fed into the main line.

21 Claims, 5 Drawing Sheets

METHOD AND APPARATUS FOR INTERMITTENT PULSATING PROPORTIONING OF A DIALYSIS FLUID MIXTURE

CROSS REFERENCE TO RELATED APPLICATIONS

This application claims priority to German application DE 10 2017 109 127.0 filed Apr. 27, 2017, the contents of such application being incorporated by reference herein.

FIELD OF THE INVENTION

The invention relates to a method for preparing dialysis fluid in which the basic component and the acid component are added to water alternately or time-shifted at least once and in an intermittent and pulsating manner so that, due to this way of addition, one single conductivity probe is sufficient to check the composition of the dialysis fluid to be mixed, wherein the addition is performed either by two pumps, by one pump including valves or by vacuum.

BACKGROUND OF THE INVENTION

In extracorporeal blood treatment, e.g. hemodialysis, hemofiltration, hemodiafiltration etc., an apparatus for preparing dialysis fluid is used which prepares the required dialysis fluid from the basic components of water, basic fluid and acid fluid. During the blood treatment of a patient the prepared dialysis fluid is passed through the dialysis-side chamber of a dialyzer through the semi-permeable membrane of which toxic substances and water are absorbed from the blood passed through the blood-side chamber of the dialyzer by diffusion (hemodialysis) or diffusion in combination with convection (hemofiltration and hemodiafiltration).

During the extracorporeal blood treatment, the dialysis fluid flushes the patient's blood to be treated in the dialyzer. The basic component of the dialysis fluid usually is a substrate containing sodium hydrogen carbonate ($NaHCO_3$) and the second component (SK) usually is a solution containing sodium chloride (NaCl), potassium chloride (KCl), magnesium chloride ($MgCl_2$), calcium chloride ($CaCl_2$)), glucose ($C_6H_{12}O_6$) and acetic acid ($CH_3COOH$) and/or citric acid ($C_6H_8O_7$).

For preparing and, respectively, for proportioning the dialysis fluid, usually metering pumps and conductivity probes are employed. A probe measures the conductivity of the $NaHCO_3$ after addition thereof with a first metering pump (BICLF). After addition of the acid component with a further metering pump, another probe measures the conductivity of the entire dialysis fluid (ENDLF).

In the case of conductivity-controlled proportioning the amounts to be added are regulated by way of the conductivities measured. In the case of volumetric proportioning, the conductivity probes merely serve for checking as the proportioning is performed directly via the metering pump delivery rates. However, this requires the exact knowledge of the composition of the components used.

DESCRIPTION OF THE RELATED ART

Usually, for preparing dialysis fluid two metering pumps and at least two conductivity probes are employed. Accordingly, a first component, basic or acid, is admixed via a first metering pump and the second component, acid or basic, is admixed via a second metering pump to high-purity water. The addition of the respective components is checked by a respective conductivity probe. For safety-related control of the composition, additionally a second independent passage and a third conductivity probe are usually provided. Rotary valve piston pumps and diaphragm pumps which excel by delivering intermittently are frequently used as metering pumps.

The use of plural metering pumps, usually two, and plural conductivity probes, usually two to three, for mixing dialysis fluid according to the method of conductivity-controlled proportioning is related with high financial expenditure, as metering pumps and conductivity probes are expensive components of an apparatus for extracorporeal blood treatment and the service life thereof moreover is limited by wear.

SUMMARY OF THE INVENTION

It is therefore an object of the present invention to overcome the known drawbacks in preparing dialysis fluid for extracorporeal blood treatment and to provide, for the preparation of dialysis fluid from high-purity water, a basic component and an acid component, a method and an apparatus (device) which excel by the fact that mixing and proportioning of the dialysis fluid is carried out in a significantly more efficient manner and thus the lump-sum and current costs for the apparatus and the method are considerably reduced.

According to aspects of the invention, this object is achieved by the combination of features of the independent claims.

Hence it is a basic idea of aspects of the invention to reduce the required technical expenditure when designing an apparatus and carrying out a method for preparing dialysis fluid that is used in extracorporeal blood treatments with constant technical reliability.

In other words, the apparatus according to aspects of the invention manages, as compared to the state of the art, with a smaller number of expensive sensory components and the method according to aspects of the invention is designed such that efficient use is made of the measuring and controlling capacity of the installed components assisted by mathematical methods so that use of additional technical measuring and control means is superfluous and, respectively, an additional measuring instrument is completely replaced.

It can be stated that the total number of measuring instruments, e.g. measuring sensors, required is reduced and, respectively, a plurality of measuring instruments common in prior art is replaced by skillfully arranging one single measuring instrument in combination with an appropriate process version.

Concretely speaking, the downsizing of the technical equipment of an apparatus for preparing dialysis fluid is provided such that for checking and controlling the method for preparing dialysis fluid only one single measuring instrument for taking at least one physical and/or chemical parameter, e.g. a conductivity probe, is used. Where needed, the technical equipment of the apparatus can be further reduced by using a maximum of one (metering) pump for delivering (supplying) the required dialysis fluid components, namely high-purity or osmotic water (hereinafter referred to as water) and a basic component (hereinafter also referred to as basic fluid) and an acid component (hereinafter also referred to as acid fluid). The addition of the two fluids to the water, i.e. the preparation of the dialysis fluid, is carried out by the operation of a (possibly single) (metering) pump and/or the control of valves and is implemented alternately, time-shifted at least once, however. Due to this method, it is possible to perform the measurement of the at least one physical and/or chemical parameter of the water-fluid mixture (also referred to as component mixture) by one single measuring device, as in the measuring instrument for the water-fluid mixture, after adding initially a first fluid from among the basic and acid fluids to the water while comparing the measured actual value to predefined target values, the dosage and, respectively, delivery rate (supply rate) of said first fluid can be checked and set or controlled and e.g. a reference value can be established for the water-fluid mixture comprised of water and the added first fluid. Upon preferred taking of the reference value, the second fluid from among the basic and acid fluids can be fed to the water-fluid mixture, either alternately with the first fluid, wherein no reference value is required in this case as both fluid-water mixtures are metered individually and separately, or in addition to the first fluid with a comparison to the reference value, without checking of the water-fluid mixture being restricted by one single measuring instrument.

In total, advantages according to aspects of the invention are achieved by dispensing with at least one measuring instrument as compared to the known apparatuses and methods for preparing dialysis fluid for use in extracorporeal blood treatment, thus rendering the expenditure for providing an apparatus for the preparation of dialysis fluid more economic and consequently also reducing the costs of the method. Since sensors are expensive to purchase, a considerable financial amount can be saved in relation to the overhead when at least one of said parts is dispensed with. Moreover, sensors have to be maintained and replaced from time to time so that, apart from the monetary expenditure, also the time for servicing needed by staff members is reduced. Furthermore, the omission of components implies a reduction of dead storage capacity and a reduced risk of failure of the apparatus due to wear.

An object is achieved by an apparatus (device) for preparing dialysis fluid for use in extracorporeal blood treatment comprising a main line for the supply of water, preferably osmotic or high-purity water, in the course of which an acid fluid and a basic fluid are fed at a particular dosage and delivery rate, respectively, wherein the dosage or delivery rate is set by a control and regulating unit as a function of at least one chemical and/or physical parameter, preferably the conductivity, of the water-fluid mixture and the at least one chemical and/or physical parameter is detected by a measuring instrument, especially a conductivity measuring probe, characterized in that a first, preferably single, measuring instrument is arranged at a portion of the main line located downstream of each of the feeding point for the acid fluid and of the feeding point for the basic fluid, and the control and regulating unit is designed to control the feeding of the acid fluid and the basic fluid at least temporarily (for the metering operation) so that over a predetermined period of time or a predetermined interval only one fluid of the acid and basic fluids is fed to the main line.

In other words, an object is achieved by an apparatus for preparing dialysis fluid which constitutes a water-fluid mixture comprised of water and a basic fluid and an acid fluid for use in extracorporeal blood treatment comprising one (single) measuring instrument for detecting at least one physical and/or chemical parameter of the water-fluid mixture, wherein the measuring instrument at least at the beginning of the procedure (metering operation) establishes at least one parameter of a water-fluid mixture initially during isolated addition of a first fluid from among the acid and basic fluids and, based thereon, optimally sets the dosage/delivery rate of said first fluid. After that, for the water-fluid mixture which at this point in time is comprised of two components preferably a reference value can be established, before the second fluid from among the acid and basic fluids is fed into the water-fluid mixture and at least one parameter, which is comparable to the reference value so as to determine deviations due to the addition of the fluid and to appropriately set the dosage/delivery rate thereof, of the water-fluid mixture then being comprised of three components is established. Alternatively, it is also possible, however, to interrupt delivery (supply) of the first fluid and to deliver (supply) the second fluid so as to separately set the dosage/delivery rate thereof in an optimum way, whereupon the first fluid with the delivery rate set before is connected again. It is possible in this way to check the mixture of water and two fluids by one single measuring instrument. The water-fluid mixture and, respectively, individual components thereof can be delivered (supplied) via known delivery means (supply means) such as pumps, in combination with valves where necessary.

It is already provided in a sufficient and preferred manner that one single pump for delivering the basic fluid and the acid fluid is arranged on the apparatus. This may be effectuated by a shared line section, for example. The delivery of the water and of both fluids may also be effectuated via one single pump, in combination with a vacuum applied to the main line or by reducing the line cross-section of the main line, where appropriate. For this, preferably at least one valve, preferably a multiway valve, may be provided for feeding the acid fluid and/or for feeding the basic fluid to the main line. In addition, the main line may be provided with a valve, preferably a pressure control valve, that is disposed especially upstream of the most upstream feeding point for the acid fluid and the basic fluid.

Advantageously, thus at least one measuring instrument and at least one pump can be saved. When reducing the number of pumps, the valves enable individual delivery rates for the components of the water-fluid mixture as the delivery rate of the shared pump and the valve opening and closing periods of the valves can be appropriately combined.

Further preferred, another measuring instrument may be provided directly downstream of the first measuring instrument and may be adapted to detect at least one physical and/or chemical parameter of the water-fluid mixture flowing through the main line.

In order to quickly and reliably identify conspicuous or faulty measuring results as such, the parameters measured by the first measuring instrument are compared to the parameters measured by the further measuring instrument. The further measuring instrument is connected to a separate monitoring unit. In other words, the measuring results of the first measuring instrument are checked by a second measurement by the further measuring instrument, thus increasing the safety in preparing the dialysis fluid.

Further preferred, the apparatus may include at least one mixing unit, preferably a static mixer or a chamber of a chamber-based balancing system, and the mixing unit may be disposed preferably downstream of the first and/or further measuring instrument and, further preferred, downstream of each of the feeding point for the acid fluid and the feeding point for the basic fluid.

The mixing of the water-fluid mixture after adding the basic fluid and/or the acid fluid in a mixing unit results in a more representative, namely more accurate, measuring result at the measuring instrument, because fluctuations in concentration due to diffusion after adding the basic fluid and/or the acid fluid to the water are homogenized and thus compensated during mixing. The mixer used may be a static mixer such as a Kenics mixer, or the chamber of a chamber-based balancing system. Mixing or homogenizing of the fluid mixture immediately downstream of the adding point (s) promotes the accuracy of the measuring results of the measuring instrument, as turbulences formed during the mixing operation will be eliminated as completely as possible over an as long flow path as possible between the discharge from the mixing unit and the passing of the measuring instrument. The arrangement downstream of the further measuring instrument is especially advantageous, when the addition of the basic fluid and/or of the acid fluid is encoded, for example via the conductivity. The basic fluid typically has a lower conductivity than the acid fluid. In order to be able to detect the conductivity of the fluid mixture passing the measuring instrument, especially the time profile of the conductivity, as accurately as possible, the water-fluid mixture should not flow through any mixing unit before passing the measuring instrument. In order to reduce fluctuations in concentration as far as possible for the further procedure and, respectively, use of the dialysis fluid prepared, however, mixing is provided in such case after the fluid mixture has left the measuring instrument.

Of preference, the apparatus may be adapted to carry out the method described in the following.

Moreover, the invention relates to a method for preparing dialysis fluid that is comprised of the three components of water and basic fluid and acid fluid for use in extracorporeal blood treatment in an apparatus for extracorporeal blood treatment comprising the steps of Delivering (supplying) water, preferably osmotic or high-purity water, through a main line, delivering (supplying) a basic fluid and feeding the same at a feeding point into the main line, delivering (supplying) an acid fluid and feeding the same at a feeding point into the main line, measuring at least one physical and/or chemical parameter, preferably conductivity and especially preferred temperature-compensated conductivity, of the water-fluid mixture that is comprised of water, the acid fluid and/or the basic fluid with a first measuring instrument, preferably a conductivity probe and especially preferred a temperature-compensated conductivity probe, and setting the delivery rates for the water, the acid fluid and/or the basic fluid by a control and regulating unit as a function of the detected measuring value, wherein the at least one physical and/or chemical parameter is measured with a preferably single measuring instrument being arranged at a section of the main line located downstream of each of the feeding point for the acid fluid and the feeding point for the basic fluid, and in that the control and regulating unit at least temporarily controls the feeding of the acid fluid and/or the basic fluid so that over a predetermined period of time or a predetermined interval only one fluid (a first fluid) from among the acid fluid and the basic fluid is fed into the main line and the parameter for setting the dosage/delivery rate of said one fluid is measured intermittently or continuously.

Preferably, at first the parameter of the water-fluid mixture containing only the one fluid (the first fluid) is measured and, based thereon, the dosage or delivery rate of said one fluid (the first fluid) is determined, wherein thereupon the feeding of said one fluid (the first fluid) is interrupted and instead the other fluid (a second fluid) from among the acid and basic fluids is fed, wherein the parameter of the water-fluid mixture containing only the other fluid (the second fluid) is measured and, based thereon, the dosage or delivery rate of said other fluid (the second fluid) is determined and finally both fluids (the first fluid and the second fluid) are fed at the afore-determined dosages or delivery rates. Alternatively preferred, the parameter of the water-fluid mixture containing only the one fluid (the first fluid) is measured and, based thereon, the dosage or delivery rate of said one fluid (the first fluid) is determined and set, with the related parameter being recorded as a reference value, whereupon the second fluid is connected to the water-fluid mixture and the parameter deviation from the reference value is established and, based thereon, the dosage or delivery rate of the second fluid is determined and set.

In other words, in the method according to aspects of the invention for preparing dialysis fluid for use in extracorporeal blood treatment in an apparatus for extracorporeal blood treatment the composition of the water-fluid mixture, which is comprised of high-purity water, a basic component and an acid component and corresponds to the dialysis fluid, is checked and controlled by way of the at least one physical and/or chemical parameter measured, wherein initially a first fluid from among the basic and acid fluids is fed into the water in an isolated manner and the water-fluid mixture consisting of two components, namely water and the first fluid from among the basic and acid fluids, is measured before the second fluid from among the basic and acid fluids is fed into the water and, respectively, the water-fluid mixture consisting of two components and is measured. Measuring of the at least one physical and/or chemical parameter of the water-fluid mixture comprised of water, the basic fluid and/or the acid fluid is carried out exclusively at a flow point which is located in the flow direction of the water downstream of the feeding point for the basic fluid and of the feeding point for the acid fluid into the main line.

The fluids are added to the water and, respectively, the water-fluid mixture in a preferably intermittent and pulsating manner, hence the fluids are delivered intermittently. This has an advantageous effect on the mixing with the water and, respectively, the water-fluid mixture. Further, due to this manner of addition, one single measuring instrument is sufficient to check the composition of the dialysis fluid to be mixed. Advantageously, at least one measuring instrument generally used in prior art can be saved in this way.

Of preference, delivering and feeding of the basic fluid (at the afore-determined dosage or delivery rate) and delivering and feeding the acid fluid (at the afore-determined dosage or delivery rate) can be alternated, especially continuously alternated. Of preference, the delivery rates of the water and/or of the delivered fluid can be newly set and adapted with each cycle and especially preferred at any time of delivery. Also, while the delivery rate of one mixture component (e.g. the conveyed fluid) is varied, the delivery rate of the simultaneously delivered component (e.g. water) set before can be maintained.

In a first alternative, the delivery of the basic fluid (at the afore-determined dosage or delivery rate) and the delivery of the acid fluid (at the afore-determined dosage or delivery rate) can take place time-shifted in parallel.

The start of delivery and the initially isolated feeding of initially one fluid from among the basic and acid fluids into the water and adaptation of the delivery rate of said one fluid and/or the water to a defined target value for the water-fluid mixture will help to calculate and/or set the required delivery rate of the one fluid and/or of the water more reliably and quickly than in the case of simultaneous delivery and simultaneous start of delivery of the basic fluid and the acid fluid and feeding into the water. After the first fluid from among the basic and acid fluids has been fed into the water and the water-fluid mixture has been measured, as a first alternative a reference value for said one fluid addition can be recorded. Subsequently, the second fluid can be additionally added to the water-fluid mixture metered before and the parameter deviations from the reference value resulting therefrom that are used as a basis of the dosage/delivery rate of the second fluid can be detected.

As a second alternative, the delivery of the first fluid can be interrupted after having completed the setting of the dosage/delivery rate thereof and can be replaced with the delivery of the second fluid. As soon as the dosage/delivery rate thereof is set by measuring of the parameter, the first fluid can be connected again with the dosage/delivery rate set before. In this way, when the second fluid from among the basic and acid fluids is subsequently fed into the water-fluid mixture, the delivery rates of all of the three mixture components, namely water, the basic fluid and the acid fluid, can be checked with one single measuring instrument.

Of preference, when a delivery rate of one fluid from among the basic and acid fluids is adapted, for the period of adapting, especially from varying the delivery rate to reaching the new target value of the water-fluid mixture, the delivery rate of the other fluid from among the basic and acid fluids set before the adaptation can be maintained or the delivery thereof can be suspended.

Especially preferred, the adaptation of a delivery rate of one component can be performed while the delivery rates of the simultaneously delivered other components are maintained. This applies especially to the event of parallel delivery of the two fluids.

The delivery rate to be varied can be set more reliably and quickly when during resetting the delivery rate to be reset constitutes the only changed variable in the water-fluid mixture. In this way, it is also possible to adapt a delivery rate for one component, while the delivery of the two other components is continued with the delivery rates set before. This applies especially to the event of parallel delivery of the two fluids.

According to aspects of the invention, the comparison to the target value includes a control. During control the actual value is compared to the target value. The deviation is formed and is subsequently transmitted to a controller which then establishes a corresponding actuating variable (in this case a pump delivery rate). For example, discontinuous multistep controllers, P controllers, PI controllers, PID controllers, fuzzy controllers, adaptive controllers, hybrid controllers and/or controllers based on artificial neuronal networks are taken into account as controllers. The target delivery rates can be established by calculation or else by analytical processes.

Further preferred, the water-fluid mixture can be passed by the apparatus for extracorporeal blood treatment, when at least one target value for the water-fluid mixture is varied or reset, up to reaching of the target value at least for the first time. This may also be applied for isolated checking of the individual dosages and, resp., delivery rates at regular intervals. This helps to prevent an otherwise threatening alkalosis or acidosis of the patient. After such short-term interruption of the delivery and addition of the basic and/or acid fluid, the one fluid whose delivery and addition were interrupted can be additionally delivered and added to such extent that in the long-term average the physiological composition to be achieved continues to result for the fluid mixture.

Basically, all relevant procedural parameters, for example mixing ratios of the components, electrolyte concentrations in the mixture, pH value of the mixture, pump volume and/or delivery volume can be considered as target values.

Of preference, in a case in which for reaching at least one target value of the water-fluid mixture a defined period of time is exceeded and/or a delivery rate exceeding a defined limit is set, a warning notice is output at the apparatus for extracorporeal blood treatment.

In this way, a wrong fluid can be prevented from being inadvertently connected to the apparatus and the connection of the fluid can be ensured to be correct. Moreover, it can be detected in this way whether the receiving tank, for example a canister, of the connected fluid is empty and has to be replaced. A warning signal may be acoustic, visual or haptic, for example.

Further preferred, the method may further include a step of measuring of at least one physical and/or chemical parameter of the water-fluid mixture that is comprised of water, the basic fluid and/or the acid fluid with a further measuring instrument, preferably a conductivity probe and especially preferred a temperature-compensated conductivity probe, which is arranged on the main line directly downstream of the first measuring instrument, and that in a case in which a deviation between the parameter measured at the first measuring instrument and the parameter measured at the further measuring instrument exceeds a defined limit a warning notice is output at the apparatus for extracorporeal blood treatment.

Another measurement, also referred to as check measurement, serves for checking the measurement performed at the first measuring instrument and is intended to increase the safety when preparing the water-fluid mixture and, respectively, the dialysis fluid. Possible first and further measuring instruments are, apart from conductivity probes, preferably those including a temperature sensor, also ion-selective electrodes or optical measuring means, for example instruments for laser-induced plasma spectroscopy.

Of further preference, the water-fluid mixture that is comprised of water, the basic fluid and/or the acid fluid can be mixed with at least one mixing unit, preferably a static mixer.

This serves for homogenization of the fluid mixture and results in more accurate and more reliable measuring results. Imaginable mixing units are, for example, Kenics mixers or chambers of chamber-based balancing systems. When the method is implemented without any mixer, for more accurate determination of the measuring value an averaging or, respectively, filtering of the measured parameters, e.g. conductivity, can be carried out with analogous or digital filtering.

Preferably, the mixing unit may be a chamber of a chamber-based balancing system and the physical and/or chemical target value of a water-fluid mixture being comprised of water, the basic fluid and/or the acid fluid may be defined so that it can be realized, by calculation, within a time unit corresponding at most to a balancing chamber switching.

In this way, a mixing in the balance chamber can be better realized. In cases in which the physical and/or chemical target value cannot be realized within a time unit which at most corresponds to a balancing chamber switching, the target value can be approached in plural stages, wherein one single target value step can be defined so that it can be realized, by calculation, within a time unit which at most corresponds to a balancing chamber switching.

Especially preferred, the addition of the basic fluid and of the acid fluid may be encoded, preferably by using a Barker code.

When the basic fluid is added, the conductivity to be achieved and, respectively, the sodium concentration to be achieved is lower at the measuring instrument than the conductivity to be achieved and, respectively, the sodium concentration to be achieved when the acid fluid is added. The signal and, respectively, the measuring value of the basic fluid then may be encoded, corresponding to the Barker code, by "−1" and the signal and, respectively, the measuring value of the acid fluid may be encoded by "+1". The signal resulting at the measuring instrument then can be processed or developed by appropriate mathematical means wherefrom the added amounts of the individual fluids can be concluded.

Of preference, the method can be adapted to be implemented in the afore-described apparatus.

The afore-described methods are based on the conductivity-controlled proportioning of the fluid mixture and, respectively, the dialysis fluid. It is also possible, as a matter of course, to prepare the dialysis fluid according to the principle of volumetric proportioning, if the pump delivery rates and the composition of the fluids are exactly known. The measurement of the at least one physical and/or chemical parameter is performed by only one measuring instrument even with this principle. The at least one physical and/or chemical parameter measured merely serves for checking and not as an actual value of a control.

BRIEF DESCRIPTION OF THE DRAWINGS

The invention is best understood from the following detailed description when read in connection with the accompanying drawings. Included in the drawings are the following figures.

DETAILED DESCRIPTION OF PREFERRED EMBODIMENTS

Figure 1:
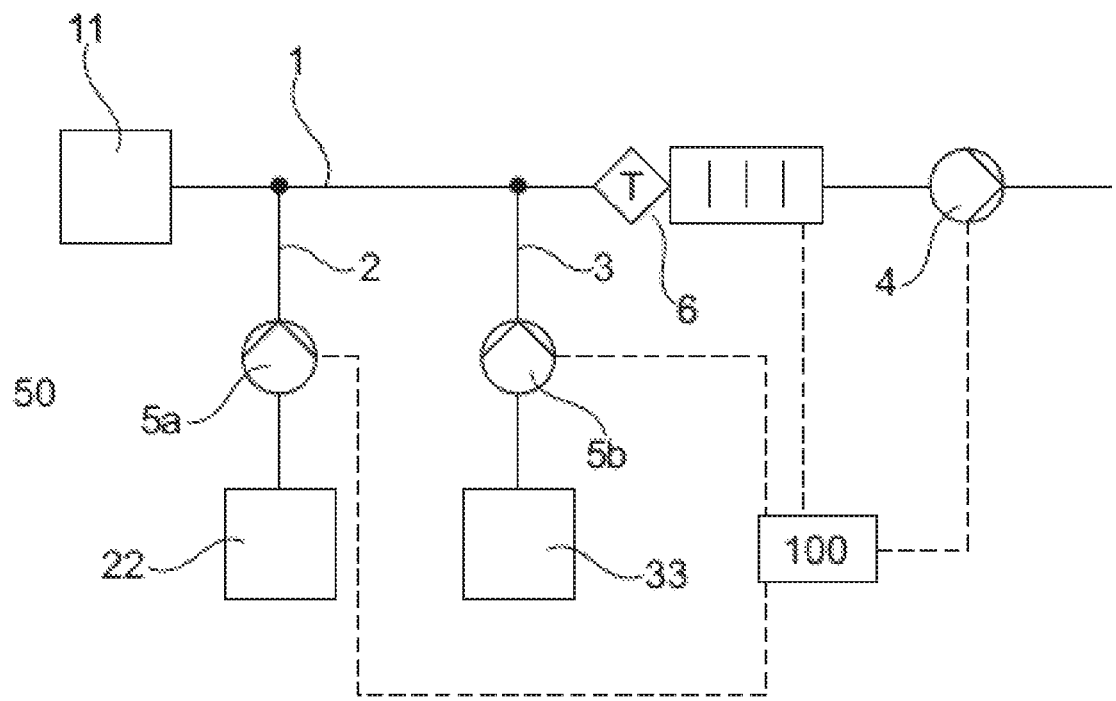
FIG. 1 illustrates a schematic representation of a first apparatus according to aspects of the invention.

FIG. 1 illustrates a first embodiment according to aspects of the invention of the apparatus for preparing dialysis fluid. A (first) variable pump 4 delivers/sucks water from a reservoir 11, which may be a container such as a canister or a continuous source, via a main line 1 in the direction of the pump 4. A (second) (metering) pump 5a arranged at a feed line 2 delivers a basic fluid from a receiving tank 22, which may be, inter alia, a canister or a cartridge, via the feed line 2 toward the main line 1 where the feed line 2 opens into the main line 1. A (third) (metering) pump 5b arranged at a further feed line 3 delivers an acid fluid from a receiving tank 33, which may be, inter alia, a canister, via the feed line 3 toward the main line 1 where the feed line 3 opens into the main line. The basic fluid and the acid fluid are added to the water by operation of the (metering) pumps 5a and 5b. Downstream of the port of the feed line 3 into the main line 1 a measuring instrument 6 is arranged which may be, inter alia, a conductivity probe, preferably a conductivity probe including a temperature sensor for temperature-compensated conductivity determination. The measuring instrument 6 measures at least one physical and/or chemical parameter of the water-fluid mixture flowing past the measuring instrument. The signals of the measuring instrument 6 are processed and the pumps 4, 5a and 5b are controlled by a control and regulating unit 100.

Figure 2:
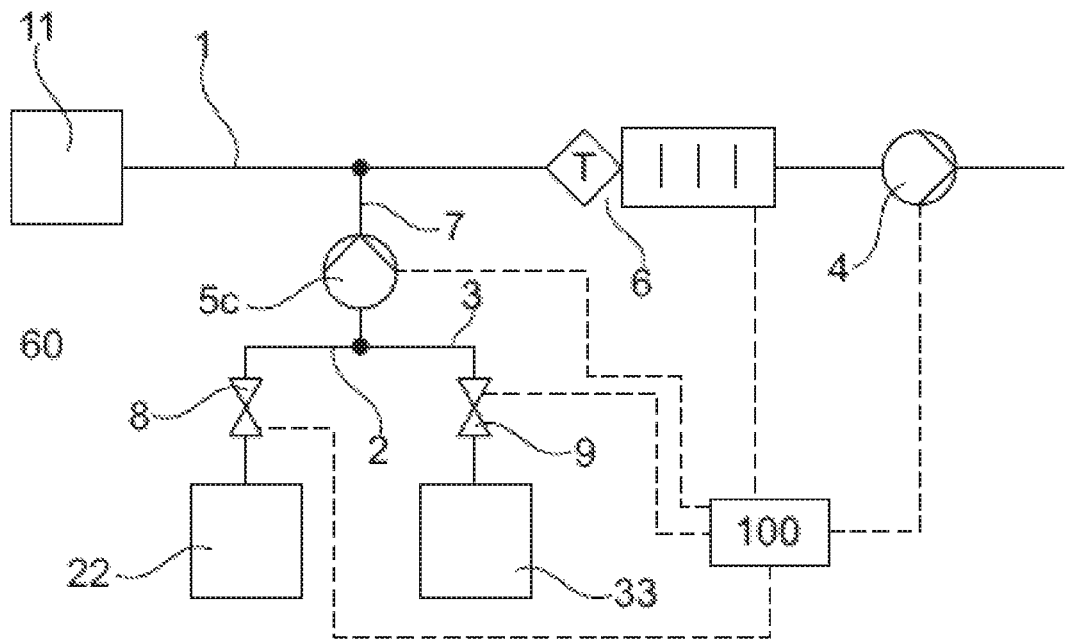
FIG. 2 illustrates a schematic representation of a second apparatus according to aspects of the invention.

FIG. 2 illustrates a second embodiment according to aspects of the invention of the apparatus for preparing dialysis fluid. The basic structure and the reference numerals from the first embodiment remain unchanged so that in the following only the differences between the first and second embodiments will be discussed. Instead of the (metering) pumps 5a and 5b, a (second) (metering) pump 5c delivers the basic fluid and the acid fluid toward the main line 1, wherein the feed line 2 and the feed line 3 converge in a shared line section 7 at which the pump 5c is arranged and the shared line section 7 opens into the main line 1. At the feed line 2 a (controllable) valve 8 is provided and at the feed line 3 a (controllable) valve 9 is provided. The addition of the basic fluid and of the acid fluid into the water is carried out by operating the (metering) pump 5c in combination with opening and closing the valves 8 and 9. Downstream of the port of the shared line section 7 into the main line 1, the measuring instrument 6 is arranged. The signals of the measuring instrument 6 are processed and the pumps 4 and 5c as well as the valves 8 and 9 are controlled by a control and regulating unit 100.

Figure 3:
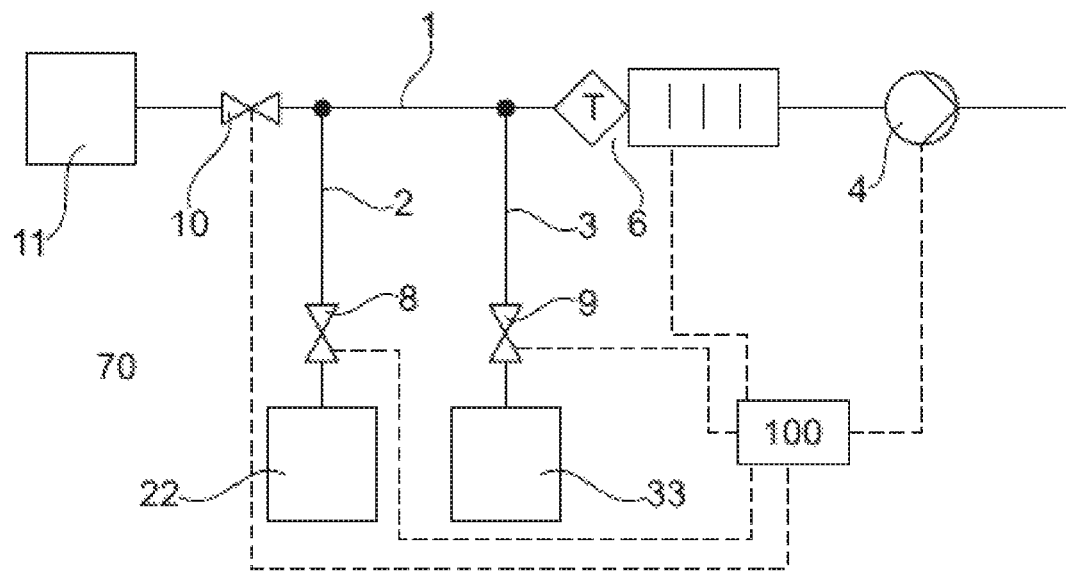
FIG. 3 illustrates a schematic representation of a third apparatus according to aspects of the invention.

FIG. 3 shows a third embodiment according to aspects of the invention of the apparatus for preparing dialysis fluid. The basic structure and the reference numerals from the first embodiment remain unchanged so that in the following only the differences between the first and third embodiments will be discussed. The basic fluid and the acid fluid are delivered by inducing a vacuum by the pump 4. For generating a vacuum, the controllable valve 10 arranged at the main line 1 and ahead of the port of the feed line 2 into the main line 1 is closed or at least the flow cross-section of the main line 1 is reduced with an appropriate valve. When at least one from among the valve 8 arranged at the feed line 2 and the valve 9 arranged at the feed line 3 is opened, the basic fluid and/or the acid fluid is/are sucked toward the main line 1 by the vacuum generated. In order to deliver the water, the valve 10 is opened so that, due to the vacuum, the basic fluid is sucked toward the pump 4. By a control and regulating unit 100 the signals of the measuring unit 6 are processed and the pump 4 as well as the valves 8, 9 are controlled. Preferably, the vacuum generated is limited to −100 to −150 mmHg, especially preferred the limitation of the vacuum depends on the difference in height between the ports of the feed line 2 and the feed line 3 into the main line 1 and the receiving tanks 22 and 33 of the basic fluid and of the acid fluid.

In the second and third embodiments, metering is carried out by the interaction of the (metering) pump and the valves so that, when one of the fluids is to be delivered and fed, the corresponding (metering) pump is operated and the valve disposed at the feed line of the fluid to be delivered is opened. Meanwhile, the valve disposed at the other feed line remains closed. When both fluids are intended to be added in parallel, this can be equally implemented by the appropriate control of the pump(s) and/or valves. In the variant of a shared (metering) pump for the fluids in combination with valves at the two feed lines, plural operating modes are possible. In a first operating mode, the delivery rate of the pump may be maintained constant for both fluid additions so that the valves have different opening times. In a second operating mode, the opening times of the valves may be maintained constant and the delivery rate of the pump may be adapted depending on which of the fluids is to be delivered. In a third operating mode, the first and second operating modes are combined so that both the pump delivery rate and the valve opening times can be varied.

Figure 4:
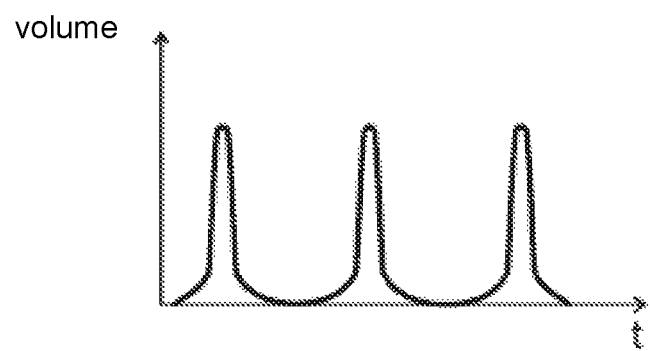
FIG. 4 illustrates a diagram of a pulsating pump delivery known from prior art.

FIG. 4 illustrates a diagram that shows an added amount (volume) as a function of time (t). In this case, a pulsating and intermittent delivery known from prior art is concerned in which the added amounts of the basic and, respectively, acid components are not fed uniformly but in a pulsated manner.

Figure 5:
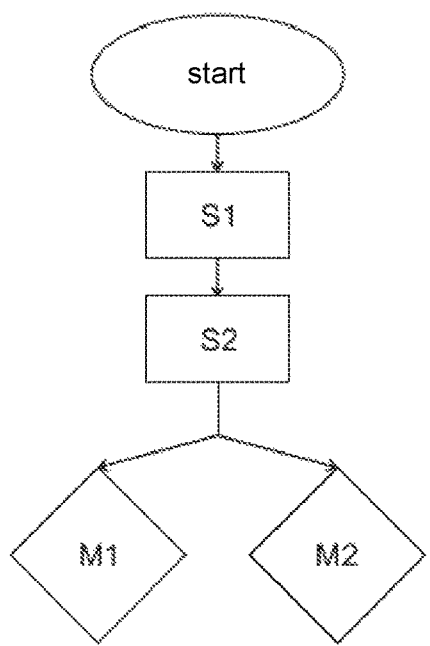
FIG. 5 illustrates a schematic representation of the method according to one aspect of the invention.

FIG. 5 illustrates a schematic representation of the (metering) process according to one aspect of the invention. After starting the process, at first the at least one physical target value and/or chemical target value are defined for a water-fluid mixture that is comprised of water, the basic fluid and/or the acid fluid and the appropriate delivery rates of the water, the basic fluid and/or the acid fluid are set. Setting may be performed by calculation, analytical determination or any other definition. This corresponds to the process step S1. Subsequently, water is delivered by the set delivery rate. This corresponds to the process step S2. After that, either in a mode M1 or in a mode M2 the basic fluid and the acid fluid are delivered and fed to the water. In the following, the modes M1 and M2 will be explained in detail in the descriptions of the FIGS. 6 and 7.

Figure 6:
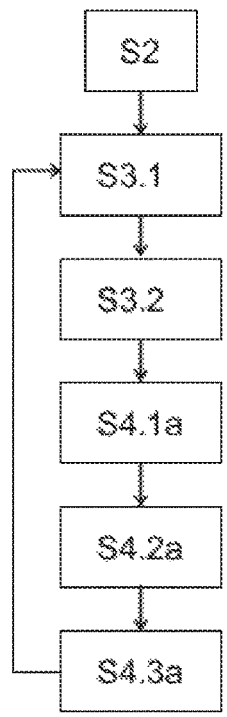
FIG. 6 illustrates a schematic representation of a first mode of metering according to aspects of the invention.

FIG. 6 illustrates a schematic representation of a first mode of metered addition M1 according to aspects of the invention in which the basic fluid and the acid fluid are alternately/serially delivered and added. Based on the process step S2, which has been illustrated in detail in the foregoing description of FIG. 5, now the delivery of exclusively a first one from among the basic and acid fluids (hereinafter a first fluid) is started and the latter is fed to the delivered water. In this context, the delivery may be carried out at a set delivery rate, especially at the delivery rate set in step S1, for the first fluid. This corresponds to the process step S3.1. Subsequently, at least one physical and/or chemical parameter of the water-fluid mixture that is comprised of or contains water and the first fluid is measured and the measuring value is compared to at least one defined target value, especially defined in step S1, for the water-fluid mixture. This corresponds to the process step S3.2. In the subsequent process step S4.1a, upon reaching the at least one target value, delivery of exclusively the first fluid is interrupted and delivery of exclusively the second one from among the basic and acid fluids (hereinafter the second fluid) is started and the latter is fed into the delivered water. The delivery can be carried out at a set delivery rate, especially at the delivery rate set in step S1, for the second fluid. After that, at least one physical and/or chemical parameter of the water-fluid mixture that is comprised of or contains water and the acid fluid is measured and the measuring value is compared to the at least one defined target value, especially defined in step S1, which corresponds to the process step S4.2a. In the subsequent process step S4.3a, upon reaching the at least one target value, delivery of the second fluid is interrupted and the process is continued with step S3.1 and, respectively, the steps starting from step S3.1 are repeated. When the delivery rate for the water, the first fluid and/or the second fluid is to be varied, this can be done by measuring control at any time of the process by delivering only the component the delivery rate of which is intended to be varied.

Figure 7:
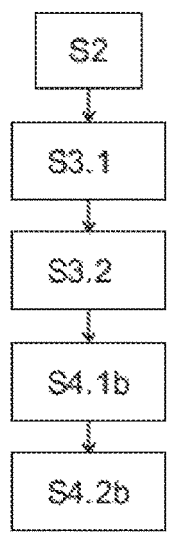
FIG. 7 illustrates a schematic representation of a second mode of metering according to aspects of the invention.

FIG. 7 illustrates a schematic representation of a second mode of metered addition M2 according to aspects of the invention in which the basic fluid and the acid fluid are delivered and added time-shifted in parallel. The mode M2 equals the afore-described mode M1 up to including step S3.2. Based on the process step S3.2, in the subsequent process step S4.1b, upon reaching the at least one target value for the water-fluid mixture that is comprised of or contains water and the first fluid, delivery of the first fluid is maintained at the delivery rate set before and the last measured parameter is retained as a reference value, whereupon delivery of the second fluid is started and the latter is fed into the water. Accordingly, delivery may be carried out at a set delivery rate, especially the delivery rate set in step S1, for the second fluid. After that, at least one physical and/or chemical parameter of the water-fluid mixture that is comprised of or contains water and both fluids is measured and the measuring value is compared to at least one defined target value, especially defined in step S1, and, respectively, to the afore-defined reference value, which corresponds to the process step S4.2b.

Figure 8:
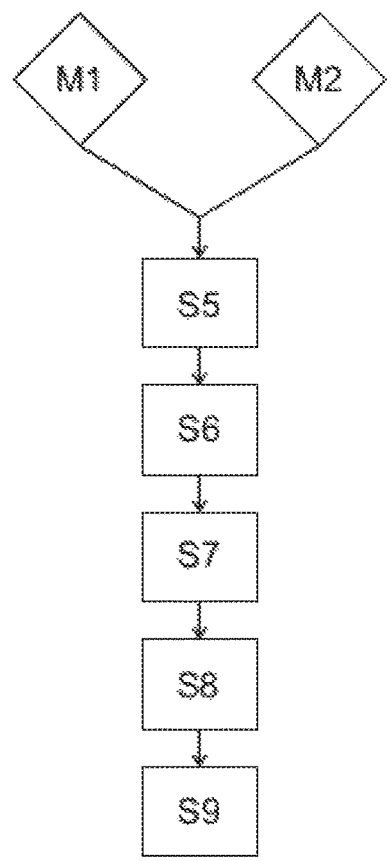
FIG. 8 illustrates a schematic representation of a mode of adapting the delivery rate according to aspects of the invention.

FIG. 8 illustrates a schematic representation of a mode M3 of the delivery rate adaptation according to aspects of the invention. Based on M2, the delivery rate of a first one from among the basic and acid fluids (hereinafter first fluid) is to be varied. For this, following the mode M2 initially the delivery of the second one from among the basic and acid fluids (hereinafter second fluid) is suspended, which corresponds to step S5. Subsequently, the first fluid is delivered at a reset delivery rate and is fed to the water-fluid mixture. This corresponds to step S6. Hereinafter, step S7 is carried out in which at least one physical and/or chemical parameter of the water-fluid mixture that is comprised of or contains water and the first fluid is measured and is compared to the new target value underlying the varied delivery rate. Subsequently, upon reaching the new target value the reset delivery of the first fluid is continued and the delivery of the second fluid is resumed and the latter is fed into the water. This corresponds to step S8. After that, at least one physical and/or chemical parameter of the fluid mixture that is comprised of or contains water and the two fluids is measured and compared to at least one defined target value, which corresponds to step S9. Then the process may be continued in either of the modes M1, M2 or M3. Alternatively, in step S5 delivery of the second fluid may be continued while maintaining the set delivery rate. In this alternative the steps S7 and S8 are omitted.

Figure 9:
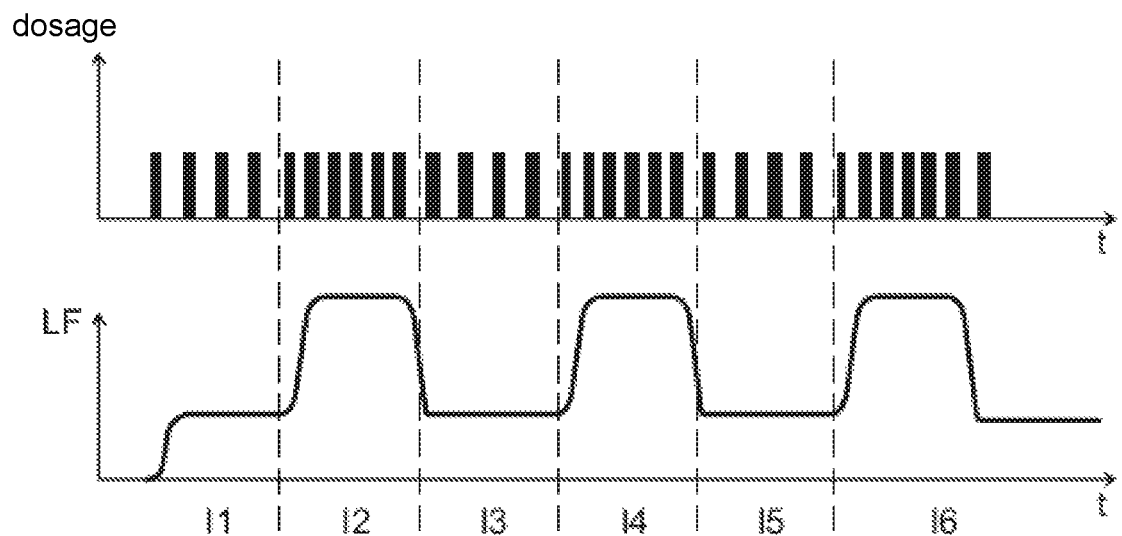
FIG. 9 illustrates a diagram of a dosage/addition method and a diagram of the measuring signal received according to one aspect of the invention.

FIG. 9 illustrates a diagram of a metering/adding method and a diagram of the measuring signal received according to one aspect of the invention. In the upper diagram, the bars in the intervals I1, I3 and I5 represent the metered volumes of the basic fluid. The bars in the intervals I2, I4 and I6 represent the metered volumes of the acid fluid. By way of said diagram it becomes evident that the metering of the fluids is performed in a pulsating manner and thus the fluid volumes are intermittently added to the first fluid.

In the lower diagram, the conductivity (LF) measured by a measuring instrument of a water-fluid mixture that is comprised of water, the basic and/or acid fluid is applied as a function of time. The basic fluid has a lower conductivity than the acid fluid. When a volume of acid fluid is measured at the measuring instrument, the conductivity signal thus is higher than when a volume of basic fluid is measured at the measuring instrument. Therefore, at the intervals at which the acid fluid is added in a pulsating manner the measured conductivity is higher than at the intervals at which the basic fluid is added.

Figure 10:
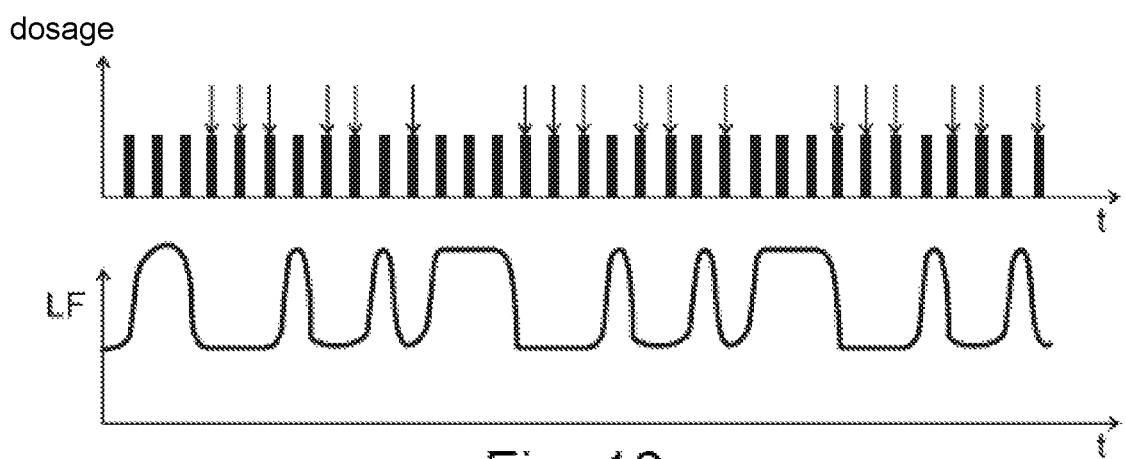
FIG. 10 illustrates a diagram of an encoded dosage/addition method and a diagram of the measuring signal received according to one aspect of the invention.

FIG. 10 illustrates a diagram of an encoded metering/adding process and a diagram of the received measuring signal according to one aspect of the invention. The arrow-marked bars in the upper diagram represent the metered volumes of the basic fluid and the unmarked bars represent the metered volumes of the acid fluid. Accordingly, the coding as described here is not restricted to the alternating delivery of the basic fluid and the acid fluid (e.g. in the mode M1), as the high conductivity ("+1") also can be achieved by continuing delivery of the basic fluid when the acid fluid is added. The signal or the measuring value of the basic fluid can be encoded, corresponding to the Barker code, by "−1" and the signal or the measuring value of the acid fluid can be encoded, corresponding to the Barker code, by "+1". The depicted diagram shows the metering according to a Barker code of the length eleven of
"+1+1+1−1−1−1+1−1−1+1−1" or "SK SK SK BK BK BK SK BK BK SK BK", wherein "SK" may as well be "SK+BK" (e.g. in the mode M2).

In the lower diagram, the conductivity (LF) measured at a measuring instrument of a fluid mixture that is comprised of water, the basic and/or acid fluid is applied as a function of the time. The measured signal corresponds to the Barker code of the length eleven of
"+1+1+1−1−1−1+1−1−1+1−1" or "SK SK SK BK BK BK SK BK BK SK BK", wherein "SK" may as well be "SK+BK" (e.g. in the mode M2).

The signal resulting from the measuring instrument may be processed or developed by appropriate mathematical means, wherefrom the added amounts of the individual components can be concluded. The total signal, for example the total conductivity, may be additionally established by mathematical averaging. According to this principle, also other encodings such as those applied in communications engineering are imaginable.

It can also be concluded from the signal dynamics whether the functionality of the measuring instrument is still given. Due to the fact that at the beginning of a conditioning phase calibration is carried out for the individual fluids, an expected value for a difference and a ratio of the two parameters of the fluids, for example conductivity, are known. The mathematical development enables both measuring values, namely for a mixture of the basic fluid and the acid fluid, to be continuously calculated and related to each other. It can be concluded from the comparison with the original ratio that the measuring instrument is still functional. This method allows to save an existing additional measuring instrument even in state of the art apparatuses.

The invention claimed is:

1. A method for preparing dialysis fluid for use in extracorporeal blood treatment on an apparatus for extracorporeal blood treatment, the method comprising the steps of
delivering water through a main line;
feeding a basic fluid and an acid fluid into the main line at one or more feeding points to form a water-fluid mixture;
measuring at least one parameter of the water-fluid mixture that includes at least one of the water, the acid fluid, or the basic fluid with a first measuring instrument; and
setting the delivery rates for at least one of the water, the acid fluid, or the basic fluid by a control and regulating unit as a function of the detected measuring value,
wherein the at least one parameter is measured with a measuring instrument arranged at a section of the main line located downstream of the one or more feeding points;
wherein the control and regulating unit controls the feeding of the acid fluid and of the basic fluid so that over a predetermined period of time or a predetermined interval only a first fluid from among the acid fluid and the basic fluid is fed into the main line and the parameter of the water-fluid mixture containing only the first fluid is measured and, based thereon, a first dosage or delivery rate of the first fluid is determined,
wherein, after the first fluid is measured, the feeding of the first fluid is interrupted and instead a second fluid from among the acid fluid and the basic fluid is fed into the main line and the parameter of the water-fluid mixture containing only the second fluid is measured and, based thereon, a second dosage or delivery rate of the second fluid is determined, and
wherein, after the second fluid is measured, the first fluid is fed into the main line at the first dosage or delivery rate and the second fluid is fed into the main line at the second dosage or delivery rate.

2. The method according to claim 1, wherein delivering and feeding of the first fluid at the first determined dosage or delivery rate and delivering and feeding of the second fluid at the second dosage or delivery rate are alternated.

3. The method according to claim 1, wherein delivering and feeding of the first fluid at the first dosage or delivery rate and delivering and feeding of the second fluid at the second dosage or delivery rate are carried out time-shifted in parallel.

4. The method according to claim 1, wherein, while adapting a delivery rate of one fluid from among the basic and acid fluids, for the period of adapting, the delivery rate of the other fluid from among the basic and acid fluids set prior to the adaptation is maintained or the delivery thereof is suspended.

5. The method according to claim 1, wherein, when at least one target value is varied or reset, the water-fluid mixture is passed by the apparatus for extracorporeal blood treatment until the at least one target value is reached at least for the first time.

6. The method according to claim 1, wherein in an event in which, for reaching at least one target value of the water-fluid mixture, at least one of a defined time span is exceeded or a delivery rate exceeding a defined limit is set, a warning notice is output by the apparatus for extracorporeal blood treatment.

7. The method according to claim 1, wherein the method further comprises the step of:
measuring at least one parameter of the water-fluid mixture that includes at least one of the water, the basic fluid, or the acid fluid with a second measuring instrument arranged on the main line directly downstream of the first measuring instrument; and in an event in which a deviation between the parameter measured at the first measuring instrument and the parameter measured at the second measuring instrument exceeds a defined limit a warning notice is output by the apparatus for extracorporeal blood treatment.

8. The method according to claim 1, wherein the water-fluid mixture that is comprised of the water and at least one of the basic fluid or the acid fluid is mixed by at least one mixing unit.

9. The method according to claim 8, wherein the at least one mixing unit is a chamber of a chamber-based balancing system and a target value of a water-fluid mixture is defined so that it can be realized, by calculation, within a time unit corresponding at most to a balancing chamber switching.

10. The method according to claim 8, wherein the at least one mixing unit includes at least one static mixer.

11. The method according to claim 1, wherein the addition of the basic fluid and of the acid fluid is encoded.

12. The method according to claim 11, wherein the addition of the basic fluid and of the acid fluid is encoded by using a Barker code.

13. The method according to claim 1, wherein the at least one parameter is at least one of a physical parameter or a chemical parameter.

14. An apparatus for preparing dialysis fluid containing the three components of water and basic fluid and acid fluid for use in extracorporeal blood treatment, comprising:
 a main line for the supply of water in the course of which each of an acid fluid and a basic fluid are fed at a particular dosage to form a water-fluid mixture, wherein the dosage is set by a control and regulating unit as a function of at least one parameter of the water-fluid mixture; and
 at least one measuring instrument configured to detect the at least one parameter arranged on a section of the main line located downstream of each of a feeding point for the acid fluid and a feeding point for the basic fluid and the control and regulating unit controls the feeding of the acid and basic fluids such that over a predetermined period of time or a predetermined interval only one from among the acid and basic fluids is fed to the main line, wherein the apparatus is provided and adapted to implement the method according to claim 1.

15. The apparatus according to claim 14, wherein the apparatus further includes at least one pump which is provided and adapted to deliver at least one of the acid fluid or the basic fluid toward the main line.

16. The apparatus according to claim 14, wherein the feeding of at least one of the acid fluid or the feeding of the basic fluid is carried out via at least one valve.

17. The apparatus according to claim 14, wherein at the main line a valve is provided which is arranged upstream of the feeding point for the acid fluid and the feeding point for the basic fluid.

18. The apparatus according to claim 14, wherein the at least one measuring instrument includes a second measuring unit provided immediately downstream of a first measuring instrument and is adapted to detect at least one parameter of the water-fluid mixture flowing through the main line.

19. The apparatus according to claim 18, wherein the apparatus includes at least one mixing unit and the mixing unit is arranged downstream of at least one of the first or second measuring instruments.

20. The apparatus according to claim 19, wherein the at least one mixing unit is arranged downstream of the feeding point for the acid fluid and the feeding point for the basic fluid.

21. The apparatus according to claim 14, wherein the at least one parameter is at least one of a physical parameter or a chemical parameter.

* * * * *